US007829026B2

(12) United States Patent
Su et al.

(10) Patent No.: US 7,829,026 B2
(45) Date of Patent: Nov. 9, 2010

(54) MAGNETIC SEPARATION DEVICE

(75) Inventors: Chih-Hsien Su, Kaohsiung (TW); Chao-Hung Kao, Taipei (TW); Yuh-Jiuan Lin, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 374 days.

(21) Appl. No.: 12/019,386

(22) Filed: Jan. 24, 2008

(65) Prior Publication Data

US 2009/0028759 A1  Jan. 29, 2009

(30) Foreign Application Priority Data

Jul. 26, 2007  (TW) .............. 96127236 A

(51) Int. Cl.
*B01L 99/10*  (2006.01)
*G01N 15/06*  (2006.01)
*G01N 33/00*  (2006.01)
*G01N 33/48*  (2006.01)

(52) U.S. Cl. ............ 422/101; 422/100; 422/102; 422/50; 422/58; 422/68.1; 436/149; 436/174; 436/177; 436/178

(58) Field of Classification Search ........ 422/100, 422/101, 102; 436/149
See application file for complete search history.

(56) References Cited

U.S. PATENT DOCUMENTS 3,897,216 A * 7/1975 Jones .................. 422/104
4,438,068 A * 3/1984 Forrest ................. 422/61
4,895,650 A * 1/1990 Wang .................. 210/222
5,571,481 A * 11/1996 Powell et al. ............ 422/104
5,647,994 A   7/1997 Tuunanen et al.
5,705,062 A   1/1998 Knobel
5,720,377 A * 2/1998 Lapeus et al. .......... 198/346.1
5,735,387 A * 4/1998 Polaniec et al. ........ 198/690.1
6,033,574 A * 3/2000 Siddiqi ................. 210/695
6,193,892 B1 * 2/2001 Krueger et al. .......... 210/695
6,228,268 B1 * 5/2001 Siddiqi ................. 210/695
6,368,561 B1 * 4/2002 Rutishauser et al. ........ 422/99
6,455,325 B1   9/2002 Tajima
6,468,810 B1   10/2002 Korpela
6,571,934 B1 * 6/2003 Thompson et al. ......... 198/619
7,476,313 B2 * 1/2009 Siddiqi ................. 210/222
7,632,405 B2 * 12/2009 Siddiqi ................. 210/222

FOREIGN PATENT DOCUMENTS

EP  1621890  1/2006

* cited by examiner

*Primary Examiner*—Brian J Sines
(74) *Attorney, Agent, or Firm*—WPAT, PC; Justin King

(57) ABSTRACT

A magnetic separation device, comprising: at least a test tube base, for receiving at least a test tube; and a magnetic member, pivotally connected to the at least one test tube base and capable of generating a magnetic force. With the aforesaid device, the test tube being received in the test tube base can be moved toward/away from the magnetic member while the magnetic member and the test tube base are driven to rotate about a pivotal end connecting the two, and thereby, the strength of the magnetic force applied on a mixture containing in the test tube by the magnetic member is varied accordingly.

14 Claims, 5 Drawing Sheets

MAGNETIC SEPARATION DEVICE

FIELD OF THE INVENTION

The present invention relates to a magnetic separation device, and more particularly, to a device for separating magnetic particles which utilizes the rotation of a rotary mechanism to alter the relative position between a magnet and a sample cell so as to separate a trace amount of an entity of interest from a complicated mixture for purification.

BACKGROUND OF THE INVENTION

Magnetic separation device, adapted for magnetic particle purification and/or separation, can effectively separate a trace amount of an entity of interest from a compound or mixture for obtaining such entity with high purity. However, in a conventional magnetic separation process, usually a number of washing cycles are carried out after magnetic particles are separated and the unwanted liquid phases are removed, each including repetitive elution and aspiration processes. Owing to the performing of such washing cycles usually requires the test tubes to be taken out of the magnetic separation device, splashing of the contents will occur, possibly causing cross-contamination between test tubes or contamination of an operator, not to mention that it is time-consuming and inconvenient when there are a plenty of test tubes required to be taken out.

There are two types of magnetic separation device. One of which is shaped like a rod, a pen or a pipette such as those disclosed in U.S. Pat. No. 6,468,810, entitled "Magnetic particle transfer device and method", U.S. Pat. No. 5,647,994, entitled "Method and apparatus for separating magnetic particles from a solution", and U.S. Pat. No. 6,455,325, entitled "Liquid processing method making use of pipette device and apparatus for same". The aforesaid devices usually immerse a magnetic probe directly into a solution for attracting magnetic particles along with targeted bio-substances attached thereupon. Nevertheless, they are disadvantageous in that: the magnetic portion of the probe must be covered by disposable protective membrane, that although cross-contamination between solutions of different test tubes can be prevented, it is troublesome to operate. Moreover, as the separation of magnetic particle in such devices require the probe to contact with the solution directly, the purification efficiency can easily be adversely affected when the probe is contaminated and adhered by some nonspecific impurities which also might cause some damage to the intended targeted bio-substances.

Another type of magnetic separation device uses magnetic members to apply magnetic forces on solution-containing test tubes from the outside thereof, such as a non-contact magnetic separation device disclosed in U.S. Pat. No. 5,705,062, entitled "Analytical device for separating magnetic microparticles from suspensions". The aforesaid analytical device comprises: a disc-shape holder having a circular groove formed thereon; a magnet set, including a pair of magnets, both disposed on the holder and each magnet in the pair being diametrically opposite to the other magnet in the pair and arranged so that the circular groove is sandwiched between the two magnets. In addition, a rotor magazine, arranged above the holder, is configured with at least a sample cell, each capable of holding and positioning a reaction vessel right on top of the circular groove while being received between the two magnets, by which when the rotor magazine is driven to rotate, the reaction vessels lodged in the sample cells will be driven to move along the circular groove and thus pass the magnetic set at each rotation so that entities of interest can be separate from a mixture containing in the reaction vessel. Nevertheless, an additional driving device is required for driving the rotor magazine to rotate while maintaining the reaction vessel to be positioned and received between the pair of magnets of the magnetic set. As the pair of magnets are diametrically opposite relative to the reaction vessel, and the polar axes of the magnets and the longitudinal axis of the reaction vessel include an acute angle, the holder must be large enough for accommodating the magnetic set as well as for configuring the circular groove thereon that is larger enough for the reaction vessel to pass through.

Another such device is a magnetic capture rack with slidable magnetic member disclosed in U.S. Pat. No. 5,571,481. The aforesaid magnetic capture rack is composed of a housing member having a plurality of sample cells disposed as a linear array, and a slidable and detachable magnetic member. By driving the magnetic member to move in parallel to the linear array of the plural sample cells in a reciprocating manner, magnetic force of the magnetic member can be applied to or removed from the test tubes received in the sample cells according to the reciprocating movement, and thereby, trace entity of interest can be separated from mixtures in the test tubes. It is noted that there must be enough space structured inside the magnetic capture rack for housing the housing member and the magnetic member, and also for enabling the magnetic member to move in such reciprocating manner without being obstructed.

Another such device is a separation device disclosed in EP1621890, entitled "Device and method for separating, mixing and concentrating magnetic particles with a fluid and use thereof in purification methods", which comprises: a pipette set, including at least a multi-layered pipette arranged as a linear array and each multi-layered pipette being composed of compartments with different cross-section areas; and a magnet set, having at least a magnet arranged as a geometrical array matching the configuration of the pipette set as well as the shape of each multi-layered pipette. As the relative position of the pipette set and the magnet set can be varied by the motions of the magnet set as well as by the raising/descending of the pipette set, entities of interest can be separated from a mixture containing in each pipette in a layer by layer manner. However, such device is difficult to operate as it is not an easy task to maneuver the pipette set and the magnet set into matching positions, not to mention that the device must have enough space for allowing the pipette set to free from the attraction of the magnet set.

SUMMARY OF THE INVENTION

The object of the present invention is to a magnetic separation device capable of altering magnetic strength at will at any time according to specific requirements of a magnetic separation process without having the test tubes used in the device to be taken out repetitively, by which not only the processing time can be greatly reduced, but also the splashing of the content and cross-contamination can be prevented.

To achieve the above object, the present invention provides a magnetic separation device, comprising: at least a test tube base, for receiving at least a test tube; and a magnetic member, pivotally connected to the at least one test tube base and capable of generating a magnetic force; wherein, the test tube being received in the test tube base is brought to move toward/away from the magnetic member while the magnetic member and the test tube base are driven to rotate about a pivotal end connecting the two.

In an exemplary embodiment of the invention, the test tube base is configured with a plurality of tube slots, each being used for allowing the test tube to lodge therein, and the plural tube slots are arranged as a linear array radial-extending from the pivotal end acting as pivot axis.

In an exemplary embodiment of the invention, the sides of the test tube base and the magnetic member facing toward each other are planar surfaces, allowing the test tube base to juxtapose with and lean against the magnetic member and enabling distances spaced between test tubes lodged in the test tube base and magnetic member to be the same.

In an exemplary embodiment of the invention, the magnetic member comprises: a frame, pivotally connected with the test tube base for enabling the magnetic member and the test tube base to rotate about a pivotal end connecting the two so as to bring the frame to move toward/away from the test tube base, and having a plurality of slots formed thereon arranged as a liner array radial-extending from the pivotal end acting as pivot axis; and a plurality of magnets, being received in the plural slot of the frame.

In an exemplary embodiment of the invention, the amount of slots formed in the frame is equal to that of the tube slots in the test tube base, and the plural tube slots in the test tube base are disposed corresponding to the plural slots of the frame in a one-by-one manner while enabling distances spaced between each magnet and its corresponding test tube to be the same as the test tube base is moved juxtaposed to and lean against the magnetic member.

In an exemplary embodiment of the invention, the magnet is an element selected from the group consisting of permanent magnets, electromagnets and the combination thereof.

In an exemplary embodiment of the invention, each tube slot of the test tube base is configured with a clipping structure for exerting a clipping force on the test tube lodged in the slot.

In an exemplary embodiment of the invention, the clipping structure is composed of a plurality of clipping arms mounted at the wall of each tube slot, and each clipping arm comprises: a connecting arm, extending from the wall of its corresponding tube slot toward the axis of the same by a length; and a clipping block, mounted at the extending end of the connecting arm in a manner that it is protruding into the tube slot; wherein, an inner diameter included inside the clipping blocks of the plural clipping arms is small then the inner diameter of the corresponding tube slot.

In an exemplary embodiment of the invention, the clipping structure is composed of two clipping arms arranged symmetrically at two opposite sides of the corresponding tube slot.

In an exemplary embodiment of the invention, the magnetic member is designed to be a bar-like element with a length, and is structured to pivotally connect with two test tube bases respectively at the two ends thereof.

In an exemplary embodiment of the invention, the two test tube bases are enabled to pivot and lean against the same surface of the magnetic member.

In an exemplary embodiment of the invention, the two test tube bases are enabled to pivot and lean against two opposite surfaces of the magnetic member.

In an exemplary embodiment of the invention, the magnetic separation device further comprises a connecting part with two axially parallel pivot holes, for connecting the magnetic member with the test tube base in a manner that one of the two pivot hole is used for pivotally connecting to the magnetic member while another pivot hole is used for pivotally connecting to the test tube base.

In an exemplary embodiment of the invention, the magnetic member has two linear arrays of magnets, being disposed inside the magnetic member respectively along two opposite and parallel planar surfaces of the magnetic member.

In an exemplary embodiment of the invention, an anti-slip pad is arranged at the bottom of the magnetic member for providing a friction between the magnetic member and the surface where the magnetic member is placed.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
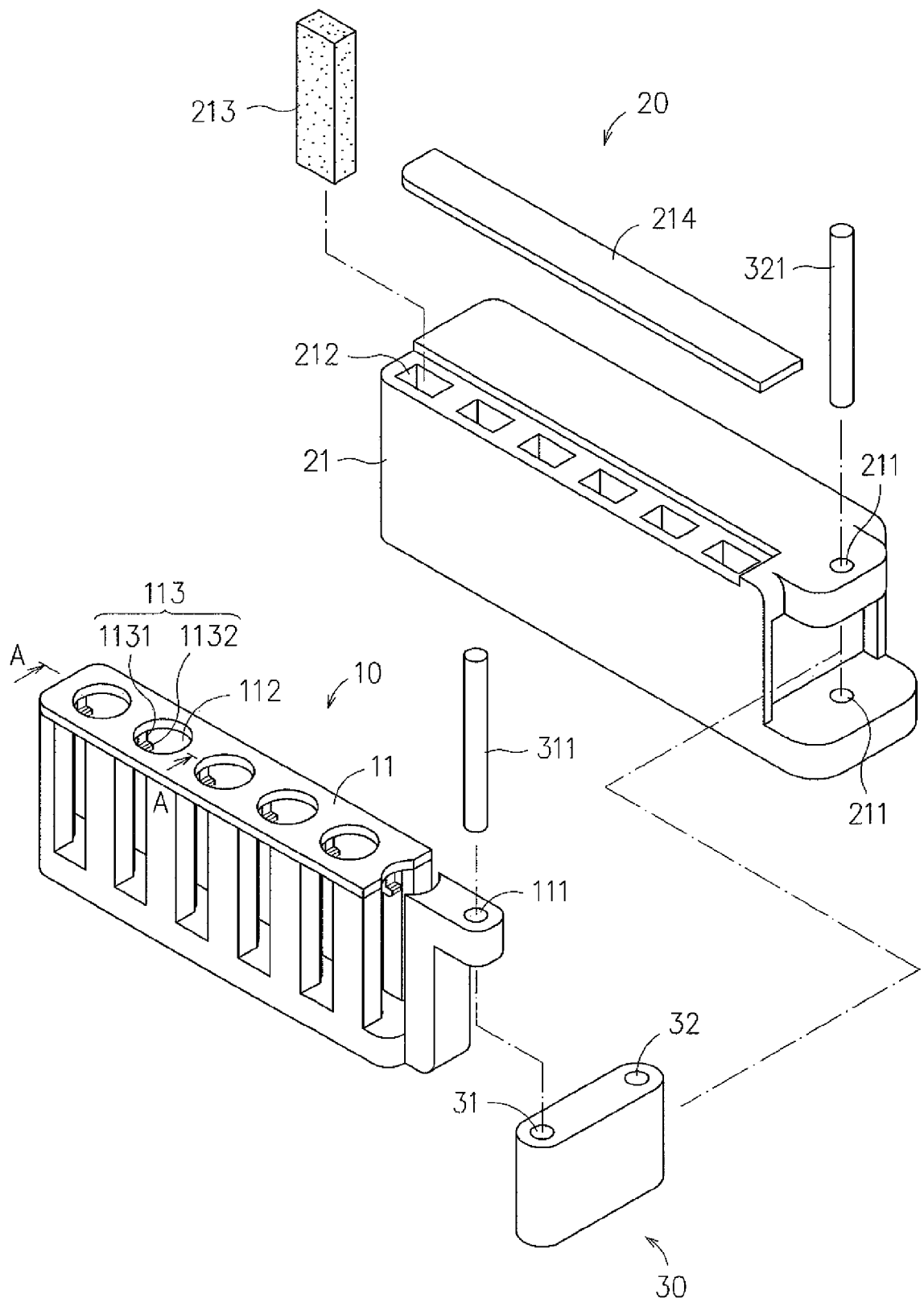
FIG. 1 is an exploded view of a magnetic separation device according to a first embodiment of the invention.
Figure 2:
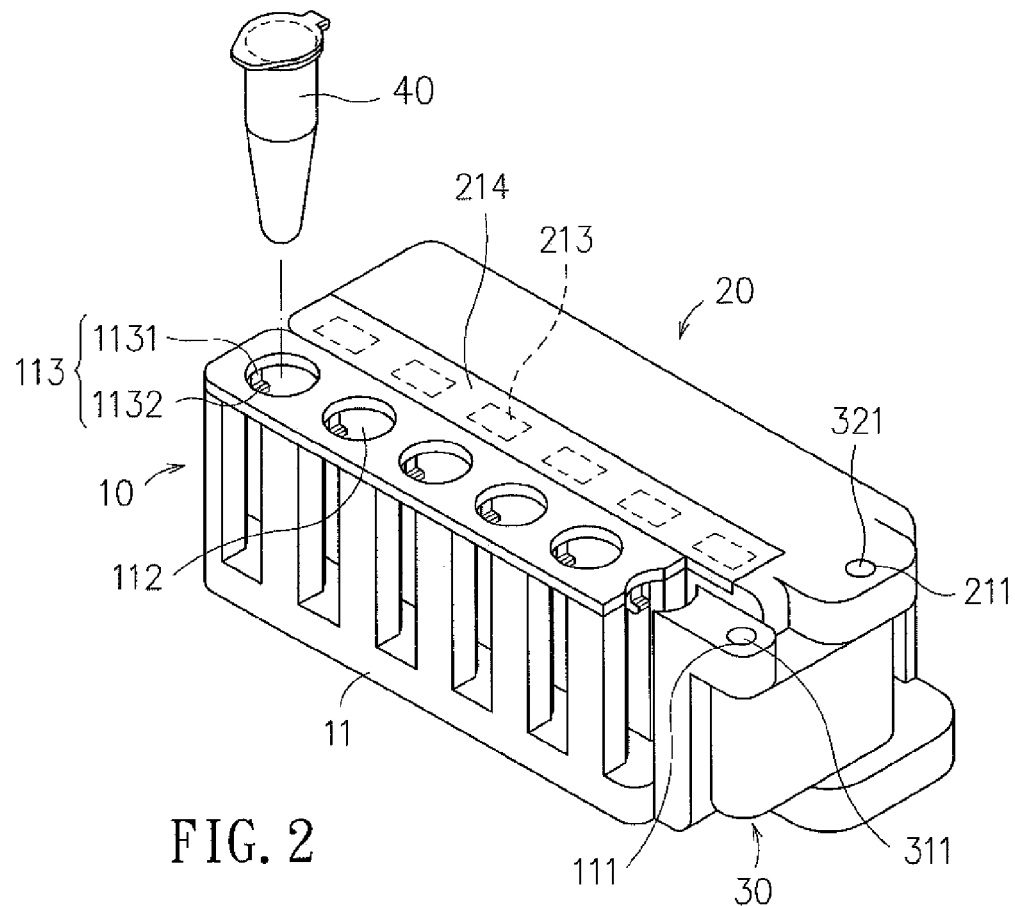
FIG. 2 shows a magnetic separation device depicted in the first embodiment of the invention.
Figure 3:
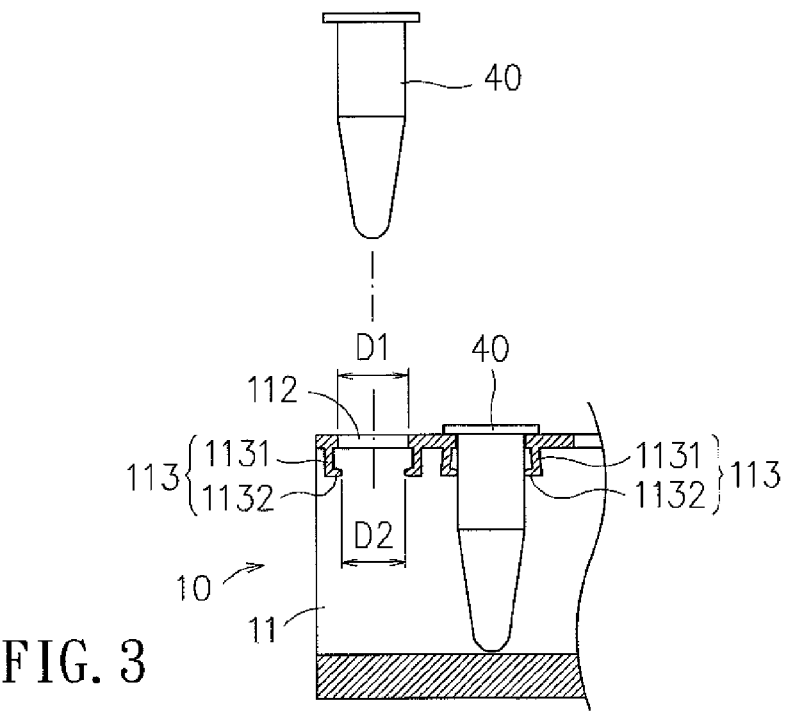
FIG. 3 is an A-A cross sectional diagram showing clipping arms of tube slots with and without test tube lodged therein.

Please refer to FIG. 1 to FIG. 3, which show a magnetic separation device according to a first embodiment of the invention. The magnetic separation device primarily comprises: a test tube base 10; a magnetic member 20; and a connecting part 30, disposed between the test tube base 10 and the magnetic member 20 while pivotally connecting thereto.

The test tube base 10 includes a base 11, which has a pivot hole 111 formed at an end thereof and is configured with a plurality of tube slots 112, each being used for allowing a test tube 40 to lodged therein as the plural tube slots 112 are arranged as a linear array radial-extending from the pivot hole 111, as shown in FIG. 2 and FIG. 3. As shown in FIG. 3, each tube slot 112 of the test tub base 10 is configured with a clipping structure, that the clipping structure is composed of two clipping arms 113 arranged symmetrically at two opposite sides of the corresponding tube slot 112. Each clipping arm 113 further comprises: a connecting arm 1131, extending from the side of the corresponding tube slot 112 where it is mounted toward the axis of the tube slot 112 by a length; and a clipping block 1132, mounted at the extending end of the connecting arm 1131 in a manner that it is protruding into the tube slot 112, whereby an inner diameter D2 included inside the clipping blocks 1132 of the two clipping arms 113 is small then the inner diameter D1 of the corresponding tube slot 112. When a test tube 40, as the one shown in the right side of FIG. 3, is inserted into the tube slot 112, the clipping arms 113 formed in that tube slot 112 are forced to bend outwardly and thus the counter-force of the bending will enable the two clipping blocks 1132 to hold and secure the test tube 40 inside the tube slot 12. It is noted that the aforesaid clipping structure of clipping arms 113 for securing test tube is only for illustration and it is obvious that the clipping structure may be varied in many ways, such as latches, elastic clips, and so on can all be used as the clipping structure, so that it is not limited by the aforesaid clipping structure of clipping arms 113.

As shown in FIG. 1 and FIG. 2, the magnetic member 20 includes a frame 21, configured with two pivot holes 211 coaxially formed at an end thereof. Moreover, there are a plurality of slots 212 formed on the frame 21 in a manner that they are arranged as a liner array radial-extending from the pivotal holes 211 acting as pivot axis. It is noted that the amount of slots 212 formed in the frame 21 is equal to that of the tube slots 112 in the test tube base 10. In the exemplary embodiment shown in FIG. 2, there are six tube slots 112 and six slots 212 and, in each slot 212, there is a magnet 213 lodged therein that each is encapsulated inside the slot by a cap 214. The magnet 213 can be a permanent magnet, an electromagnet, or the combination thereof.

The connecting part 30 is configured with two axially parallel pivot holes 31, 32. By inserting one pivotal shaft 311 into the pivot hole 31 and the pivot hole 111 of the test tube base 10 for connecting the two and then inserting another pivotal shaft 321 into the pivot hole 32 and then into the pivot hole 211 of the magnetic member 20, the test tube base 10, the magnetic member 20 and the connecting part 30 are pivotally connected with each other.

Figure 4:
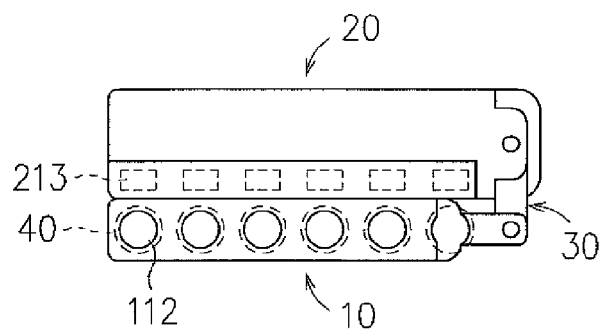
FIG. 4 is a top view of FIG. 2 as the test tube base is positioned to lean against the magnetic member.
Figure 5:
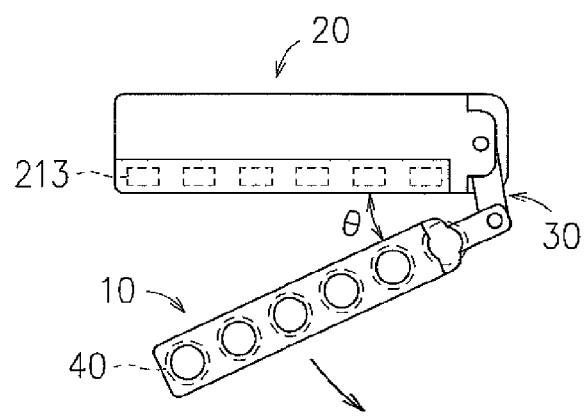
FIG. 5 is another top view of FIG. 2 as the test tube base is pivoted by an angle.
Figure 6:
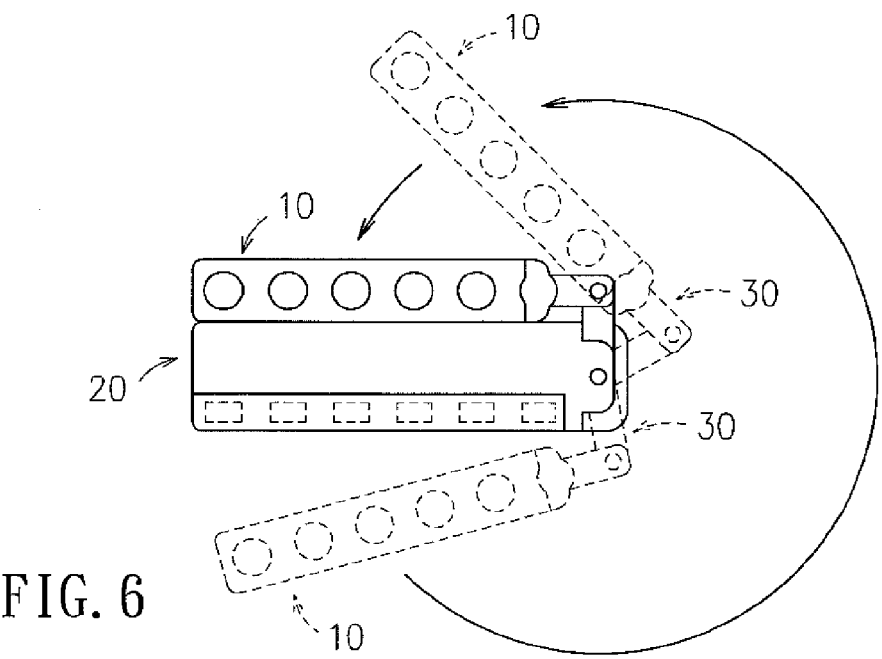
FIG. 6 is another top view of FIG. 2 as the test tube base is pivoted by 360°.

FIG. 4 is a top view of FIG. 2 as the test tube base 10 is positioned to lean against the magnetic member 20. When the test tube base 10 is positioned to lean against the magnetic member 20, the test tubes 40 in the test tube base 10 are subjected to a maximum magnetic force under the influence of the magnets 213 in the magnetic member 20. As shown in FIG. 4, as the plural tube slots 112 in the test tube base 10 are disposed corresponding to the magnets 213 in a one-by-one manner while enabling distances spaced between each magnet and its corresponding test tube to be the same as the test tube base 10 is moved juxtaposed to and lean against the magnetic member 20 so that all the test tubes 14 are subjected to corresponding magnetic forces of the same strength, and thus it is suitable for removing solution from the test tubes 40. After the solution removal process is accomplished, the test tube base 10 is pivoted to separate itself from leaning against the magnetic member 20, by which the strength of the magnetic forces influencing the test tubes 40 by the magnets 213 are decreased. As soon as the test tube base 10 is pivoted by an angle θ, all the test tubes 40 of the test tube base 10 are released from the magnetic influence of the magnets 213. In addition, if there is enough space, the test tube base 10 can be pivoted by 360° while turning the connecting part 30 by about 180° for positioning the test tube base 10 to lean against another side of the magnetic member 20 opposite to the previous side thereof, as shown in FIG. 6.

It is emphasized that the structure and size of the base 11 of the test tube base 10 as well as those of the frame 21 of the magnetic member 20 are not limited by the aforesaid embodiments and thus modifications are not to be regarded as a departure from the spirit and scope of the invention. Moreover, the amount of tube slots 112 as well as that of the slots 212 are not limited to be six, but can be any number with respect to actual requirement, only if the plural tube slots 112 in the test tube base 10 can be disposed corresponding to the slot 212 of the magnetic member 20 in a one-by-one manner. In this exemplary embodiment, the sides of the test tube base 10 and the magnetic member 20 facing toward each other are planar surfaces, allowing the test tube base 10 to juxtapose with and lean against the magnetic member 20 and enabling distances spaced between test tubes lodged in the test tube base 10 as an linear array and magnets lodged in the magnetic member 20 as an linear array to be the same.

Figure 7:
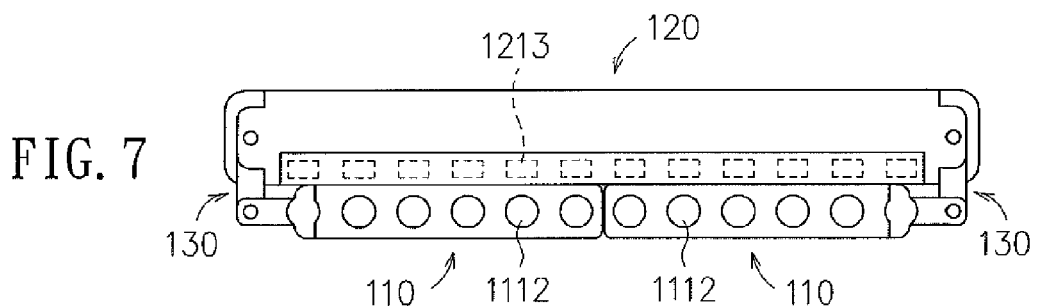
FIG. 7 shows a magnetic separation device according to a second embodiment of the invention.
Figure 8:
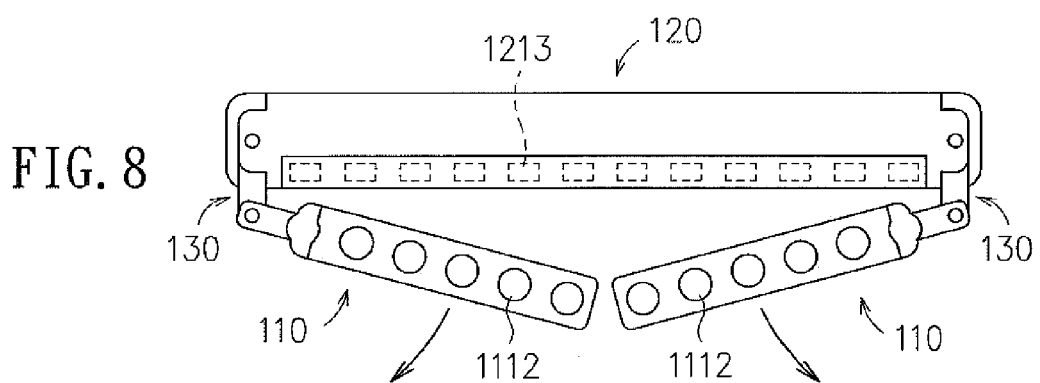
FIG. 8 is a top view of FIG. 7 as the test tube base is pivoted by an angle.

Please refer to FIG. 7 and FIG. 8, which show a magnetic separation device according to a second embodiment of the invention. In the second embodiment, the magnetic member 120 is designed to be a bar-like element with a length, and is structured to pivotally connect with two pairs of test tube bases 110 and connecting parts 130 respectively at the two ends thereof. As shown in FIG. 7, the two test tube bases 110 are positioned to lean against a same side of the magnetic member 120 in a manner that the plural tube slots 1112 in the test tube base 110 can be disposed corresponding to the magnets 1213 of the magnetic member 120 in a one-by-one manner. In FIG. 8, as the test tube bases 110 are pivoted by an angle for detaching the same from the magnetic member 120 and thus moving the tube slots 1112 away from the magnets 1213, the pivoting of the two test tube bases 110 can be performed in synchronization with each other or not. Similarly, the two test tube bases 110 can be pivoted by 360° to lean against another side of the magnetic member 120 opposite to the previous side thereof.

Figure 9:
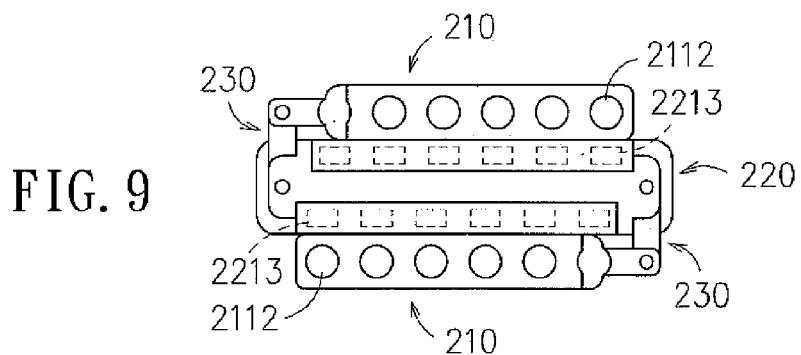
FIG. 9 shows a magnetic separation device according to a third embodiment of the invention.
Figure 10:
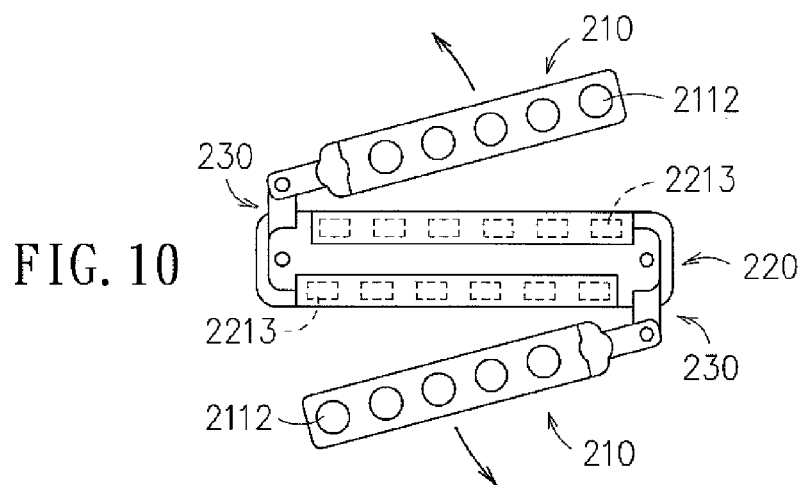
FIG. 10 is a top view of FIG. 9 as the test tube base is pivoted by an angle.

Please refer to FIG. 9 and FIG. 10, which show a magnetic separation device according to a third embodiment of the invention. In the third embodiment, the magnetic member 220 is designed to be a bar-like element with a length, and is structured to pivotally connect with two pairs of test tube bases 210 and connecting parts 230 respectively at the two ends thereof. As shown in FIG. 9, the two test tube bases 210 are positioned to respectively lean against two opposite sides of the magnetic member 220 in a manner that the plural tube slots 2112 in the test tube base 210 can be disposed corresponding to the magnets 2213 of the magnetic member 220 in a one-by-one manner. In FIG. 10, as the test tube bases 210 are pivoted by an angle for detaching the same from the magnetic member 220, the tube slots 2112 can be moved away from the magnets 2213 Similarly, the two test tube bases 210 can be pivoted by 360° for switching sides of the magnetic member 220 to lean against. It is noted that the pivoting of the two test tube bases 210 can be performed in synchronization with each other or not.

Figure 11:
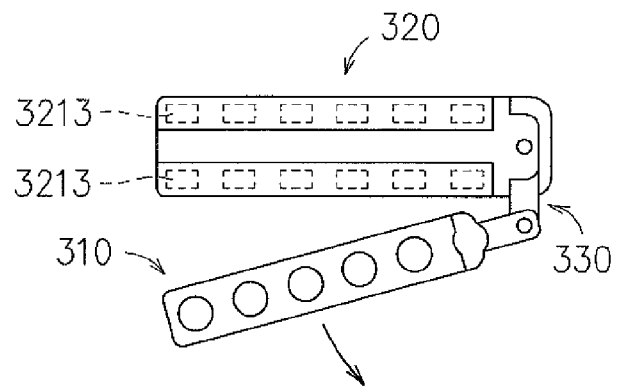
FIG. 11 shows a magnetic separation device according to a fourth embodiment of the invention as the test tube base is pivoted by an angle.
Figure 12:
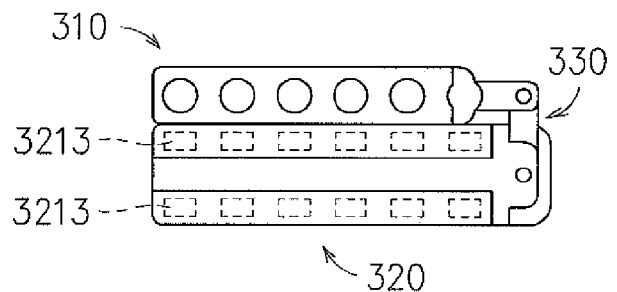
FIG. 12 shows a magnetic separation device of FIG. 11 as the test tube base is pivoted by 360°.

Please refer to FIG. 11 and FIG. 12, which show a magnetic separation device according to a fourth embodiment of the invention. In the fourth embodiment, only one pair of a test tube base 310 and a connecting part 330 is connected to an end of a magnetic member 320, and the magnetic member 320 is configured with two linear arrays of magnets 3213, being disposed inside the magnetic member 320 respectively along two opposite and parallel planar surfaces of the magnetic member 320. By pivoting the test tube base 310, the test tube base 310 can be switched between the two parallel planar surfaces for subjecting the test tubes lodged therein under influence of different arrays of magnets 3213.

Figure 13:
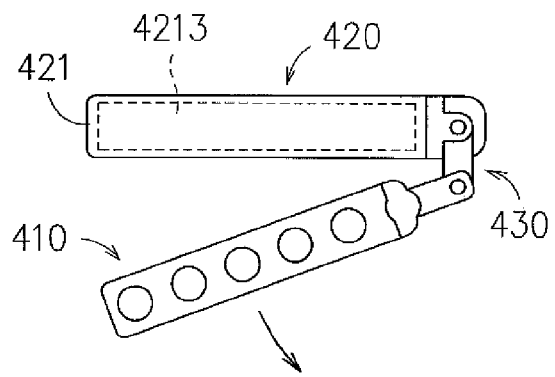
FIG. 13 shows a magnetic separation device according to a fifth embodiment of the invention as the test tube base is pivoted by an angle.
Figure 14:
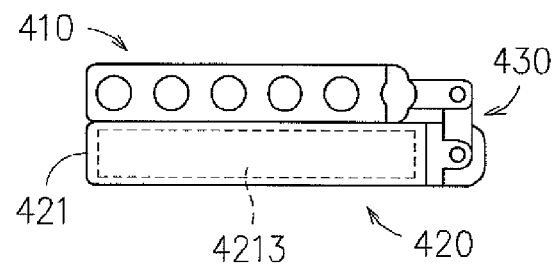
FIG. 14 shows a magnetic separation device of FIG. 12 as the test tube base is pivoted by 360°.

Please refer to FIG. 13 and FIG. 14, which show a magnetic separation device according to a fifth embodiment of the invention. In the fifth embodiment, only one pair of a test tube base 410 and a connecting part 430 is connected to an end of a magnetic member 420. However, the interior of the magnetic member 420 is filled with a block of magnet 4213. Thereby, as test tube base 410 is switching between the two opposite surfaces of the magnetic member 420, the test tubes of the test tube base 410 are subjecting to the influence of the same magnets 4213 in a manner similar to those shown in FIG. 11 and FIG. 12.

It is noted that in all the aforesaid embodiments, there can be an anti-slip pad, arranged at the bottom of the magnetic member for providing a friction between the magnetic member and the surface where the magnetic member is placed, and thus facilitating the test tube base to pivot about the connecting part.

To sum up, the magnetic separation device of the invention is a device capable of utilizing the rotation of a rotary mechanism to alter the relative position between magnets and corresponding test tubes, by which not only a simple magnetic screen effect can be achieved when the magnet is moved away from the sample cell, but also the miniaturization of the whole magnetic separation device is achievable. As the magnetic separation device of the invention is able to alter its magnetic strength applying on a test tube at will at any time according to specific requirements of a magnetic separation process, the washing cycle in the magnetic separation process can be performed without having the test tube to be taken out repetitively, and thereby, the process time can be greatly reduced and also the chances of splashing and cross-contamination are eliminated. In addition, as the rotations of the two bases are reversible, the device is able to apply magnetic force on the test tube again for removing magnetic particles after entities of interest had be eluted.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A magnetic separation device, comprising:
    at least a test tube base, for receiving at least a test tube; and
    a magnetic member, pivotally connected to the at least one test tube base and capable of generating a magnetic force;
    wherein, the test tube being received in the test tube base is brought to move toward/away from the magnetic member while the magnetic member and the test tube base are driven to rotate about a pivotal end connecting the two; and the test tube base is configured with a plurality of tube slots, each being used for allowing the test tube to be lodged therein, and the plural tube slots are arranged as a linear array radial-extending from the pivotal end acting as pivot axis.

2. The magnetic separation device of claim 1, wherein the sides of the test tube base and the magnetic member facing toward each other are planar surfaces, allowing the test tube base to juxtapose with and lean against the magnetic member and enabling distances spaced between test tubes lodged in the test tube base and magnetic member to be the same.

3. The magnetic separation device of claim 2, wherein the magnetic member further comprises:
    a frame, pivotally connected with the test tube base for enabling the magnetic member and the test tube base to rotate about a pivotal end connecting the two so as to bring the frame to move toward/away from the test tube base, and having a plurality of slots formed thereon, arranged as a liner array radial-extending from the pivotal end acting as pivot axis; and
    a plurality of magnets, being received in the plural slot of the frame.

4. The magnetic separation device of claim 3, wherein the amount of slots formed in the frame is equal to that of the tube slots in the test tube base, and the plural tube slots in the test tube base are disposed corresponding to the plural slots of the frame in a one-by-one manner while enabling distances spaced between each magnet and its corresponding test tube to be the same as the test tube base is moved juxtaposed to and lean against the magnetic member.

5. The magnetic separation device of claim 3, wherein the magnet is an element selected from the group consisting of permanent magnets, electromagnets and the combination thereof.

6. The magnetic separation device of claim 1, wherein each tube slot of the test tub base is configured with a clipping structure for exerting a clipping force on the test tube lodged in the slot.

7. The magnetic separation device of claim 6, wherein the clipping structure is composed of a plurality of clipping arms mounted the wall of each tube slot, and each clipping arm further comprises:
    a connecting arm, extending from the wall of its corresponding tube slot toward the axis of the same 5 by a length; and
    a clipping block, mounted at the extending end of the connecting arm in a manner that it is protruding into the tube slot;
    wherein, an inner diameter included inside the clipping blocks of the plural clipping arms is small then the inner diameter of the corresponding tube slot.

8. The magnetic separation device of claim 7, wherein the clipping structure is composed of two clipping arms arranged symmetrically at two opposite sides of the corresponding tube slot.

9. The magnetic separation device of claim 1, wherein the magnetic member is designed to be a bar-like element with a length, and is structured to pivotally connect with two test tube bases respectively at the two ends thereof.

10. The magnetic separation device of claim 9, wherein the two test tube bases are enabled to pivot and lean against the same surface of the magnetic member.

11. The magnetic separation device of claim 9, wherein the two test tube bases are enabled to pivot and lean against two opposite surfaces of the magnetic member.

12. The magnetic separation device of claim 1, further comprising: a connecting part with two axially parallel pivot holes, for connecting the magnetic member with the test tube base in a manner that one of the two pivot hole is used for pivotally connecting to the magnetic member while another pivot hole is used for pivotally connecting to the test tube base.

13. The magnetic separation device of claim 1, wherein the magnetic member has two linear arrays of magnets, being disposed inside the magnetic member respectively along two opposite and parallel planar surfaces of the magnetic member.

14. The magnetic separation device of claim 1, further comprising: an antislip pad, arranged at the bottom of the magnetic member for providing a friction between the magnetic member and the surface where the magnetic member is placed.

* * * * *